(12) United States Patent
Jetter et al.

(10) Patent No.: US 6,346,142 B1
(45) Date of Patent: Feb. 12, 2002

(54) SYSTEM FOR REMOVING WATER FROM A GASEOUS SAMPLE

(75) Inventors: Jeffrey Jay Jetter, Cypress; Shinji Maeshiro, Torrance; Kazumi Yamazaki, Rancho Palos Verdes, all of CA (US)

(73) Assignee: Honda Giken Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/473,307

(22) Filed: Dec. 28, 1999

(51) Int. Cl.$^7$ .............................................. B01D 53/22
(52) U.S. Cl. .................................. 96/9; 96/10
(58) Field of Search ................ 96/4, 8, 9, 10; 95/45, 52, 288; 73/23.3, 23.37

(56) References Cited

U.S. PATENT DOCUMENTS

| | | |
|---|---|---|
| 3,834,136 A | 9/1974 | Dussourd et al. |
| 3,934,989 A | 1/1976 | Haugen |
| 3,998,095 A | 12/1976 | Tinkham et al. |
| 4,467,435 A | 8/1984 | Warnke et al. |
| 4,705,543 A | 11/1987 | Kertzman |
| 4,801,805 A | 1/1989 | Butler et al. |
| 4,857,081 A * | 8/1989 | Taylor ............................ 95/52 |
| 4,928,015 A | 5/1990 | Butler et al. |
| 4,944,776 A * | 7/1990 | Keyser et al. .................. 95/52 |
| 4,958,075 A | 9/1990 | Mace et al. |
| 5,042,500 A | 8/1991 | Norlien et al. |
| RE33,678 E * | 9/1991 | Campbell et al. .............. 95/52 |
| 5,138,163 A | 8/1992 | Butler et al. |
| 5,143,695 A * | 9/1992 | van den Burg ............... 73/23.3 |
| 5,245,405 A | 9/1993 | Mitchell et al. |
| 5,473,162 A | 12/1995 | Busch et al. |
| 5,712,433 A | 1/1998 | Kojima |
| 5,731,510 A | 3/1998 | Jones et al. |
| 5,753,013 A | 5/1998 | Dingfelder |
| 5,843,209 A * | 12/1998 | Ray et al. ...................... 95/52 |
| 6,042,634 A * | 3/2000 | Van Tassel et al. ............ 95/52 |

FOREIGN PATENT DOCUMENTS

JP 55-137006 A * 10/1980

OTHER PUBLICATIONS

"Performance Of A New System For Emission Sampling And Measurement (SESAM)" By Heller et al., SAE The Engineering Society For Advancing Mobility Land Sear Air And Space, International Congress And Exposition, Feb. 26–Mar. 2, 1990, No. 900275, pp. 1–11.

"Model Measurement Of Raw Exhaust Volume And Mass Emissions By SESAM", No. 980047, pp. 61–71 (No date given).

* cited by examiner

Primary Examiner—David A. Simmons
Assistant Examiner—Frank M. Lawrence
(74) Attorney, Agent, or Firm—O'Melveny & Myers LLP (57) ABSTRACT

An improved drying system is provided for removing moisture from gases such that a sufficiently dry gaseous sample is available for accurate analyses of the constituent components. The drying system includes a series of selectively permeable drying tubes or tube bundles located in a shell, where the moisture is removed from the gaseous sample via an ionic channel that extends through the tubing walls. The selectively permeable drying tubes allow water vapor to pass through the tube walls, but prevent the adsorption of most other gases. The sample gas is drawn through the tubes, and dried air is made to pass past the tubes in a counterflow direction. The first stage of the selectively permeable drying tubes is heated to raise the dew point of the gas stream, while the later stage is cooled in order to enhance the drying efficiency of the system. In this fashion, water vapor is removed from the gaseous sample stream in a more efficient manner than is presently available.

20 Claims, 5 Drawing Sheets

SYSTEM FOR REMOVING WATER FROM A GASEOUS SAMPLE

RELATED APPLICATION DATA

This application relates to co-pending application Ser. No. 09/473,312 for SYSTEM FOR VEHICLE EMISSION SAMPLING AND MEASUREMENT, filed concurrently herewith on Dec. 28, 1999, which is incorporated by reference herein in the entirety.

BACKGROUND OF THE INVENTION

1. Field of the Invention

The present invention relates to the art of gas analysis, and more particularly, to a process and apparatus for the removal of moisture from gases to produce a sufficiently dry sample for accurate measurement of constituent elements in the gases.

2. Description of Related Art

The science of gas analysis has numerous useful applications, from the measurement of human respiratory gases to the testing of pollutant levels in the atmosphere and vehicle emissions. Historically, this analysis was accomplished by collecting the gas that was to be sampled in bags and then sampling the collected gas or collecting solids or liquids off-line from the flow of the gases being analyzed. These techniques suffered from an inability to provide instantaneous dynamic information, and generally only measured a single component per technique. Additionally, the techniques were time consuming, sometimes taking weeks to perform a single analysis. Gas analysis techniques performed without liquids or solids have included chemilluminescence, flame ionization, and total hydrocarbon analysis. The gas analysis techniques performed without liquids or solids sometimes suffered from the cross-interference of added chemicals and also the inability to test for some constituent components.

More recent technological advances have made Fourier transform infrared (FTIR) spectrometric techniques available for use in gas analysis. For example, U.S. Pat. No. 4,928,015 discloses a method of using FTIR quality control techniques for analyzing multi-component constituency in gas emission flow. An FTIR spectrometer can provide simultaneous real-time concentration measurements of exhaust gas components, and is applicable for those gases that absorb infrared radiation in a sample because of the molecular oscillations and rotations. Those gases show a specific infrared absorption at different wavelengths resulting in typical spectra. All of the spectra of gases to be analyzed by the FTIR are stored in the instruments memory, and then those reference spectra are compared with the spectra of the sample gases during analysis.

One of the chief problems faced in sampling gases using FTIR analysis is obtaining a dry sample. Any moisture in the sample can significantly alter test data. As such, it is imperative that water be removed so that the moisture will not interfere with the FTIR readings. Some methods for obtaining a satisfactory sample include heating the gas itself to a temperature in excess of 100° C. in order to maintain any water present in a vapor state, diluting the gas flow with the addition of large quantities of a non-reactive gas such as nitrogen, or passing the gas though a bank of desiccants to dehydrate it. All three of these methods have drawbacks. In the case of heating the gas to temperatures in excess of 100° C., any reference or comparative samples also have to be heated to the same temperature to achieve an accurate comparison. Furthermore, even when maintained in a vapor state, the moisture may provide interference with certain low level FTIR measurement analysis. Diluting the gas with large quantities of a non-reactive gas decreases the level of sensitivity of the sample that can be obtained due to the dilution of the sample contents, thus providing a less accurate analysis. Also, dilution requires the presence of large tanks containing the diluting gas, making a compact system difficult to achieve. And, finally, passing the sample through a desiccant bank often removes gaseous components that are desirable for testing along with the water vapor.

The most recent technological advances in the art of moisture removal include the use of selectively permeable materials to remove water vapor via ionic channels that can absorb water molecules. For instance, U.S. Pat. No. 5,042,500 discloses a drying sample line for coupling a patient's expiratory gases to a gas analyzer. The drying sample line comprises concentric tubes wherein the innermost tube is fabricated from a perflourinated polymer material sold as Nafion®. The perflourinated polymer material exhibits high permeability to water vapor but does not readily pass other gases. The expiratory gas is drawn through the inner tube and, simultaneously, dried air is made to pass through the outer tube in a counterflow direction relative to the expiratory gases. Because of the properties of the perflourinated polymer material, water vapor (i.e., moisture) contained in the expiratory gas being coupled to the analyzer passes through the wall of the tube and into the dried air stream. Consequently, the water vapor is removed from the expiratory gas mixture being applied to the analyzer.

More particularly, the perflourinated polymer material has a Teflon backbone, with periodic side chains of perflourinated ether terminating in a sulfonic acid group. These acid groups form "ionic channels" that extend through the walls of the perflourinated polymer tubing. Each sulfonic acid group can absorb up to 13 molecules of water. Where the partial pressure of the water in the sample exceeds that external to the tubing, water molecules will travel along the ionic channels and be release outside the tubing. This process is selective for water, although some other species such as alcohols, ketones and ammonia may experience some loss.

Other products on the market employ in-line systems utilizing perflourinated polymer tubing for drying gas streams. However, the present products do not lower the moisture level sufficiently for accurate testing in all applications, particularly where a compact system is required because of space limitations. A more efficient process, chiefly one that is compact enough for the needs of various testing environments, is required.

SUMMARY OF THE INVENTION

In addressing the needs and deficiencies of the prior art, a water removal system for removing moisture from a gas stream is provided.

The water removal system of the present invention comprises a plurality of drying tubes coupled together in series. The drying tubes have a first flow path for a sample gas and a second flow path for a purge gas. Both the sample gas and the purge gas flow through the drying tubes, the sample gas flowing through a first flow path, and the purge gas flowing through a second flow path. At least one of the plurality of drying tubes is disposed in a cooling chamber maintained at a reduced temperature relative to the ambient temperature of the sample gas stream. A purge air source provides the purge gas. The cooling chamber reduces the temperature of the sample gas to an approximate dew point to increase the efficiency of the drying tubes.

More particularly, the drying tubes each comprise an outer shell having a sample gas inlet and a sample gas outlet, a plurality of internal tubes comprises of a selectively permeable ion exchange polymer material are disposed within the outer shell, extending between the sample gas inlet and the sample gas outlet. The sample gas flows through the internal tubes, and the purge air flows inside the outer shell along the internal tubes. Water is removed from the sample gas inside the internal tubes via ionic channels that absorb water molecules.

A more complete understanding of the system for removing water from a gaseous sample will be afforded to those skilled in the art, as well as a realization of additional advantages and objects thereof, by a consideration of the following detailed description of the preferred embodiment. Reference will be made to the appended sheets of drawings that will first be described briefly.

DETAILED DESCRIPTION OF THE PREFERRED EMBODIMENT

The present invention satisfies the need for an efficient process for removing water from a gaseous sample. In the detailed description that follows, like element numerals are used to describe like elements illustrated in one or more of the figures.

Figure 1:
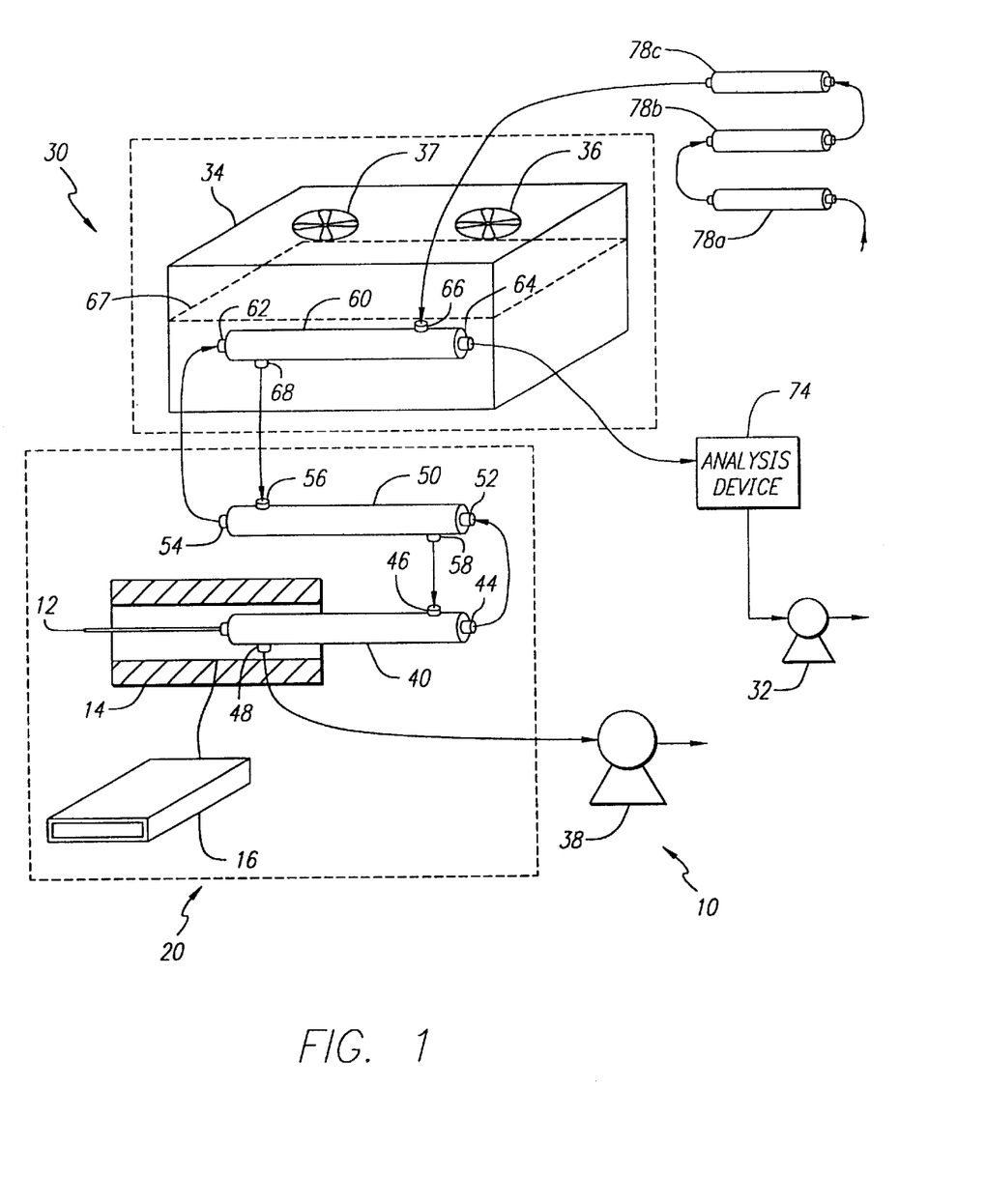
FIG. 1 is a schematic diagram illustrating a water removal system and its constituent components in accordance with the present invention.

Referring first to FIG. 1 of the drawings, the water removal system 10 comprises a heating stage 20 and a cooling stage 30. Drying occurs in both the heating stage 20 and the cooling stage 30; additionally though, the gas is either heated or cooled in order to increase the efficiency of the water removal system 10. The heating stage 20 is the foremost stage of the water removal system 10 and provides a mechanism for heating the gas. There are two reasons for heating the gas. First, the interaction of liquid water with the perflourinated polymer tubing is endothermic, and leads to a cascade failure reaction. Therefore, the gas must be kept above the dew point temperature until most of the water has been removed. Second, the initial water absorption and transport by the perflourinated polymer tubing proceeds as a First Order Kinetic reaction, in which absorption becomes more rapid with increasing temperature.

The cooling stage 30 is the latter stage of the water removal system 10 and lowers the temperature of the gas to increase the efficiency of the drying elements in the cooling stage 30. The purpose of cooling the gas is to draw more of the retained water from the sulfonic acid group, since the residual retained water becomes the limiting factor after the First Order Kinetic reaction.

More particularly, the heating stage 20 includes an inlet tube 12, a heating sleeve 14, a heater controller 16, a first stage drying tube 40, and a second stage drying tube 50. The inlet tube 12 comprises an elongated cylindrical tube that is open on both ends. The heating sleeve 14 may comprise a resistance type heater shaped in a tubular fashion such that it may be wrapped around components that are to be heated. The heating sleeve 14 is electrically connected to a heater controller 16 that regulates the temperature of the heating sleeve. Each of the first and second stage drying tubes 40, 50 comprises a bundle of selectively permeable perflourinated polymer tubes surrounded by a rigid shell, as will be further described below with respect to FIG. 2. The first and second stage drying tubes 40, 50 each includes a sample gas flow inlet 42, 52 and outlet 44, 54, and a purge gas flow inlet 46, 56 and outlet 48, 58.

The inlet tube 12 and a portion of the first stage drying tube 40 are enclosed by the heating sleeve 14. The inlet tube 12 is connected to the sample gas flow inlet 42 of the first stage drying tube 40. As shown in FIG. 1, the heating sleeve 14 includes a cylindrical portion that surrounds the inlet tube 12 and further extends to surround the foremost half of the first stage drying tube 40. The sample gas flow outlet 44 of the first stage drying tube 40 is connected to the sample gas flow inlet 52 of the second stage drying tube 50. The purge gas flow outlet 48 of the first stage drying tube 40 is connected to a purge vacuum pump 38. In a preferred embodiment of the invention, the purge vacuum pump 38 may comprise a centrifugal type pump capable of maintaining at least five inches Hg vacuum.

The cooling stage 30 comprises a third stage drying tube 60 and an ice bath 34. The ice bath 34 comprises a thermodynamically insulating material formed in a shell containing a volume of ice and water within the thermodynamic boundaries of the shell. The ice bath shell may be configured in the shape of a box and is enclosed on all six sides, but contains openings permitting the various components of the drying system 10 to pass therethrough. Further, the ice bath shell should have one or more openings to permit the replenishment of ice and the draining of water. The ice bath shell is comprised of a rigid material to maintain its shape while holding a volumetric capacity of the ice and water mixture. The third stage drying tube 60 is similar in construction to the first and second stage drying tubes 40, 50 described above, and includes a sample gas flow inlet 62 and outlet 64, and a purge gas flow inlet 66 and outlet 68. The third stage drying tube 60 is disposed within the ice bath 34 below the surface 67 of the water and The sample gas flow outlet 54 of the second stage drying tube 50 is connected to the sample gas flow inlet 62 of the third stage drying tube 60. The sample gas flow outlet 64 of the third stage drying tube 60 is connected to an analysis device 74. Accordingly, the first, second and third stage drying tubes 40, 50, 60 are each connected in series. A sample gas drawn into the sample gas flow inlet 42 of the first stage drying tube 40 will pass successively through the second and third stage drying tubes 50, 60 and ultimately be provided to the analysis device 74. The purge gas flow outlet 68 of the third stage drying tube 60 is connected to the purge gas flow inlet 56 of the second stage drying tube 50. The purge gas flow outlet 58 of the second stage drying tube 50 is connected to the purge gas flow inlet 46 of the first stage drying tube 40. A dry purge air source is provided by three desiccant tubes 78a, 78b, and 78c each containing a suitable material, such as $CaSO_4$. Each one of the desiccant tubes 78a–78c has an inlet and outlet, and the three tubes are connected in series. The purge vacuum pump 38 is connected to the purge gas flow outlet 48 of the first stage drying tube 40. The outlet of the third tube 78c is connected to the purge gas inlet 66 of the third stage drying tube 60. Accordingly, a constant flow of purge air passes through the desiccant tubes 78a–78c, and through the first, second and third drying tubes 40, 50, 60.

The analysis device 74 is adapted to measure the constituent components of a gas flowing out of the sample gas outlet 64 of the third stage drying tube 60, and may be provided by an FTIR spectrometer or other like measuring system. The analysis device 74 is connected to a vacuum pump 32 that draws the sample gas through the serially-connected first, second and third stage drying tubes 40, 50, 60. The vacuum pump 32 may be provided by a centrifugal type pump capable of maintaining at least four inches Hg vacuum. It should be appreciated that the dry gas sample from the third stage drying tube 60 could alternatively be provided to other types of systems for various purposes.

In operation, a sample gas enters the drying system 10 through the inlet tubing 12. The sample gas is drawn and maintained at a slight vacuum by the vacuum pump 32, which provides a negative pressure that permits gaseous flow through the system. The sample gas becomes heated by the heating sleeve 14 as it is flowing through the inlet tube 12. In an embodiment of the invention, the heating sleeve 14 is maintained at approximately 70° C. by operation of the heater controller 16. The sample gas travels from the inlet tube 12 to the first stage drying tube 40. The heating sleeve 14 also encloses the first half of the first stage drying tube 40 (as described above), and heats the sample gas as it travels through the drying tube 40. Moisture is removed from the sample gas by the first stage drying tube 40 as the sample gas travels through the tube in a process that will be described below. The removed moisture is withdrawn from the first stage drying tube 40 through the purge gas outlet 48.

After the gas exits the sample gas outlet of the first stage drying tube 40, it is drawn into the sample gas inlet 52 of the second stage drying tube 50. More moisture is removed from the gas by the second stage drying tube 50 as the gas travels through the drying tube. After exiting the sample gas outlet 54 of the second stage drying tube 50, the sample gas is drawn into the sample gas inlet 62 of the third drying tube 60. The third drying tube 60 is contained in the ice bath 34, which is maintained at approximately 0° C. in an embodiment of the invention. The temperature of the sample gas is lowered as it travels through the third drying tube 60 disposed in the ice bath 34. This cooling brings the sample gas closer to its dew point, which increases the efficiency of the drying tubes as will be further described below. After exiting the sample gas outlet 64 of the third drying tube 60, the now fully dried sample gas is drawn into the analysis device 74, where the sample gas is analyzed to determine its component makeup. Finally, the gas passes through the vacuum pump 32, and is exhausted from the system.

Ambient purge air is drawn into and through the system by the purge vacuum pump 38, and passes through the desiccant tubes 78a, 78b, and 78c. The purge air provides a lower moisture gaseous flow and a consequent water vapor pressure gradient so that moisture will travel via the ionic channels of the perflourinated polymer drying tubes 40, 50, 60 from the area of higher concentration moisture, i.e., the sample gas, into the area of lower moisture concentration, i.e., the purge air. After the purge air exits the third of the desiccant tubes 78c, the purge air enters the dry purge inlet 66 of the drying tube 60, and exits via the wet purge outlet 68. The purge air is maintained at a vacuum, which effectively lowers the dew point of the purge air even further, enhancing the water vapor pressure gradient and increasing the drying properties of the desiccated ambient air. The purge air is then drawn in series through the drying tube 50, and then drying tube 40, and is finally exhausted to the ambient surroundings via the purge vacuum pump 38. It should be appreciated that a different number of desiccant tubes could be advantageously utilized, and the three desiccant tubes 78a, 78b, 78c are merely exemplary of a purge air drying system.

In an embodiment of the invention, an intake fan 36 and an outtake fan 37 may be provided on the shell of the ice bath 34, such as on the top horizontal surface of the shell. The fans 36, 37 operate in opposite directions in order to draw a flow of air through the ice bath 34. Cooled air exiting the outtake fan 37 can then be used to cool nearby electrical components via convection, such as the analysis device 74. Operation of the fans 36, 37 may be regulated by a control device (not shown) to provide cooling air as needed. Also, the ice bath 34 may operate as a moisture sink in areas of high humidity to essentially pre-treat ambient air before it is drawn into the purge air drying system.

Figure 2:
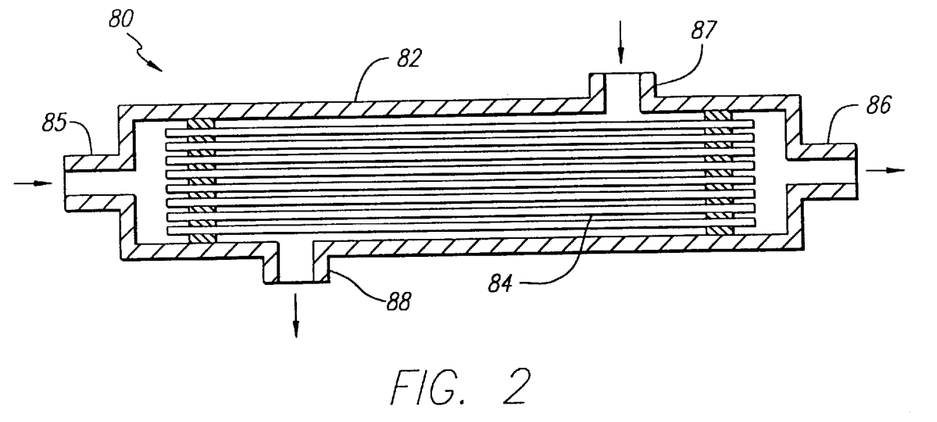
FIG. 2 is a side sectional view of an exemplary perflourinated polymer material drying tube bundle.
Figure 3:
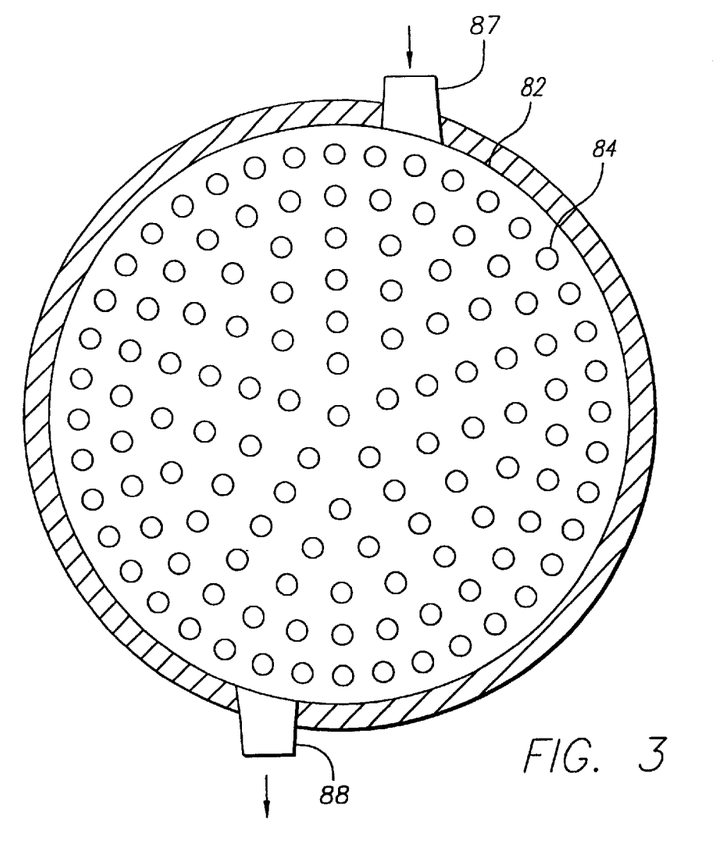
FIG. 3 is an end section view of the exemplary perflourinated polymer drying tube of FIG. 2.

FIGS. 2 and 3 show with greater particularity an exemplary drying tube 80, which provides the drying tubes 40, 50, 60 described above with respect to FIG. 1. In a preferred embodiment of the invention, the drying tube may be provided by a PD series gas dryer manufactured by Perma Pure, Inc., of Toms River, N.J. The exemplary drying tube 80 contains a perflourinated polymer material, but it should be appreciated that any substance comprising an ion exchange material exhibiting a selectively high permeability to transfer of water vapor compared to other gaseous compositions would serve the same purpose. The drying tube 80 comprises an elongated cylindrical shell 82 made of a rigid plastic or metal material. The shell 82 further includes a sample gas inlet 85 comprising a small protruding cylindrical tube extending from a first axial end thereof, and a sample gas outlet 86 comprising a small protruding cylindrical tube extending from the opposite end of the shell. A purge gas inlet 87 is located on the outer surface of the shell 82 and comprises a small cylindrical tube extending outwardly in a radial direction. Similarly, a purge gas outlet 88 is located on the opposite outer surface of the shell 82 and comprises a small cylindrical tube extending outwardly in a radial direction.

The shell 82 contains therein a bundle of selectively permeable perflourinated polymer plastic tubes 84 that extend axially through the shell 82. The perflourinated polymer plastic tubes 84 are coupled at respective ends to form a manifold at either end. As shown in FIG. 3, spaces may be provided between each respective one of the perflourinated polymer plastic tubes 84 to permit the flow of moisture from the sample gas into the purge gas. Further, a space may be provided between the sides of the shell 82 and the outermost ones of the perflourinated polymer plastic tubes 84. The shell 82 and perflourinated polymer tubes 84 allow for flow of two separate gas streams. The sample gas flows along the perflourinated polymer tubes 84 and water vapor passes through the sides of the perflourinated polymer tubes. The purge gas flows past the perflourinated polymer tubes 84 in the bundle and carries water vapor from the sample gas into the purge gas stream.

More particularly, FIG. 2 shows the flow path of the sample and purge gases in the exemplary drying tube 80. The sample gas enters through the inlet 85, and flows through the bundle of perflourinated polymer plastic tubes 84 in an axial direction, and then exits via the outlet 86. While the sample gas is flowing through the perflourinated polymer plastic tubes 84, a purging gas enters through the dry purge inlet 87 and flows through the shell 82 in a counterflow direction to the sample gas travelling in the tube bundle. The purge gas then exits via the wet purge outlet 88. Because of the moisture permeability properties of the perflourinated polymer tubes 84, water vapor contained within the sample gases passes through the walls of the perflourinated polymer tubes via ionic channels that absorb water molecules and into the dried air stream flowing through the shell 82. As known in the art, the perflourinated polymer material is selectively permeable. As a result, the other components of the sample gas are retained in the perflourinated polymer tubes.

It is important that the purge gas have a moisture content that is less than that of the sample gas. While a parallel type flow pattern could be used, a counter-flow exchange has been chosen because it is considered more efficient. Even utilizing a counter-flow exchange, however, the level of moisture removal achieved by merely passing the air samples through the perflourinated polymer tubes 84 alone is considered insufficient to lower the moisture content low enough to achieve a sufficiently accurate gas analysis. Therefore, the present invention includes the heating stage 20 and the cooling stage 30 to change the temperatures of the gas sample at their respective stages to enhance the drying properties of the system. First, the heating stage 20 maintains the moisture in the sample gas in a vapor state by raising the temperature of the gas above the dew point. Then, the cooling stage 30 lowers the temperature of the sample gas just prior to it entering the analysis device 74 so that the gas temperature is nearer the dew point. The sequentially staged drying tubes included in the respective heating and cooling stages 20, 30 ensure that the sample gas reaching the analysis device 74 is as close to completely dry as possible.

Figure 4:
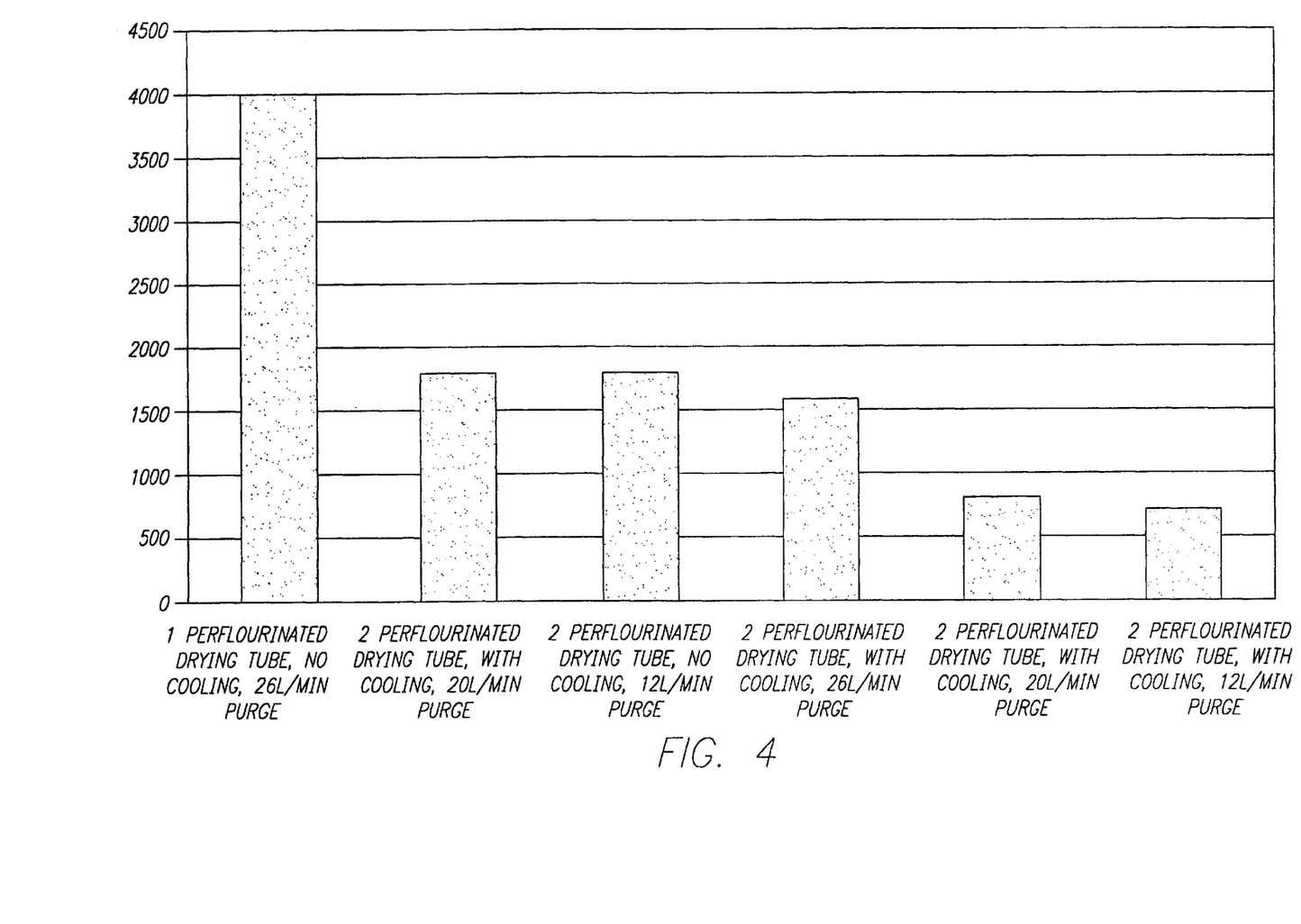
FIG. 4 is a graph illustrating the relative efficiency of moisture removal for different system configurations.

FIG. 4 shows a graph illustrating the relative efficiency of moisture removal for different system configurations. Nitric oxide was used as a sample gas to obtain the data for the graph. The x-axis of the graph displays various drying system configurations, while the y-axis displays the level of moisture remaining in the gas in parts per million (ppm). The first column of the graph shows a drying system having a single drying tube with no cooling and a purge rate of 26 L/min reduces moisture content of the sample gas to approximately 4,000 ppm. The second column of the graph shows a drying system having a single drying tube with cooling and a purge rate of 20 L/min reduces moisture content of the sample gas to approximately 1,800 ppm. The third column of the graph shows a drying system having two drying tubes with no cooling and a purge rate of 12 L/min reduces moisture content of the sample gas to approximately 1,800 ppm. The fourth column of the graph shows a drying system having a single drying tube with cooling and a purge rate of 26 L/min reduces moisture content of the sample gas to approximately 1,600 ppm. The fifth column of the graph shows a drying system having two drying tubes with cooling and a purge rate of 20 L/min reduces moisture content of the sample gas to approximately 800 ppm. The sixth column of the graph shows a drying system having two drying tubes with cooling and a purge rate of 12 L/min reduces moisture content of the sample gas to approximately 700 ppm. As is apparent from these test results, the most efficient moisture removal efficiencies are possible when a cooling stage is added to the drying system.

Figure 5:
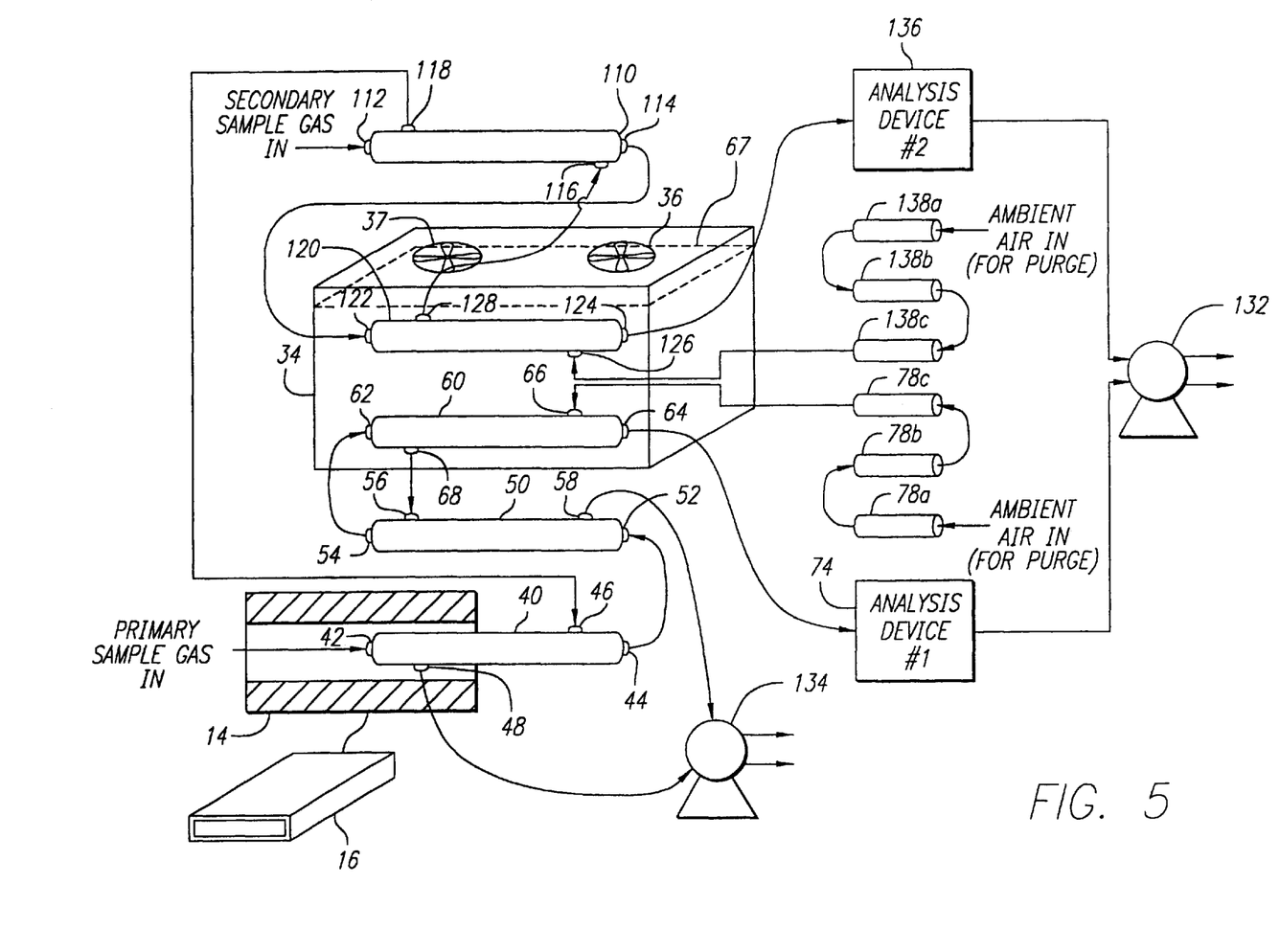
FIG. 5 is a schematic drawing illustrating a second alternative embodiment of the invention in which two separate gas streams are dried simultaneously.

Referring now to FIG. 5, a second embodiment of the present invention is provided for drying two separate gas samples simultaneously, referred to as a primary and a secondary gas stream. The secondary drying system is intended to remove vapor from samples wherein the water content is above the dew point temperature for a given ambient condition, such as during most weather conditions. The second embodiment includes many components similar to those found in the first embodiment of the invention. The secondary drying system includes a first stage secondary drying tube 110 and a second stage secondary stage drying tube 120. Additionally, three additional desiccant tubes 138a, 138b, and 138c have been added. Finally, the vacuum pumps 32 and 38 of the first embodiment of the invention have been substituted with double-head vacuum pumps 132, 134. The primary gas stream passes through the drying tubes 40, 50, and 60, and is provided to a first analysis device 74 in the same manner described above.

More particularly, the sample gas inlet 112 of the first stage secondary drying tube 110 receives a secondary gas stream. The sample gas outlet 114 of the first stage secondary drying tube 110 is connected to the sample gas inlet 122 of the second stage secondary drying tube 120. The second stage secondary drying tube is 120 is disposed in the ice bath 34 along with the third stage primary drying tube 60. The sample gas outlet 124 of the second stage secondary drying tube 120 is coupled to a second analysis device 136. The purge gas inlet 126 of second stage secondary drying tube 120 is coupled to the three serially coupled desiccant tubes 138a, 138b, and 138c. The purge gas outlet 128 of the second stage secondary drying tube 120 is connected to the purge gas inlet 116 of the first stage secondary drying tube 110. The purge gas outlet 118 of the first stage secondary drying tube 110 is connected to the purge gas inlet 46 of the first stage primary drying tube 40, which is in turn connected to the vacuum pump 134 through the purge gas outlet of the first stage primary drying tube. Both the first and second analysis devices 74, 136 are coupled to the vacuum pump 132.

The secondary sample gas enters the system and is drawn by the double-head vacuum pump 132 into the wet sample inlet 112 of the first stage drying tube 110, and exits via the dry sample outlet 114. The secondary sample gas is then drawn into the wet sample inlet 122 of the second stage drying tube 120 which is located in the same ice bath 34 as the third stage drying tube 60 utilized for drying the primary sample gas. The secondary sample gas is then drawn to the analysis device. The double head vacuum pump 132 provides the motive for both the primary and secondary gas streams.

The ambient purge air utilized in the second embodiment shown in FIG. 5 follows a slightly different route than it does in the first embodiment shown in FIG. 1. The ambient purge air follows one of two paths, either as purge air for the secondary sample gas or for the primary sample gas. Both streams are drawn by the double-head purge vacuum pump 134. The purge air stream for the primary gas sample stream, after being dried in its bank of desiccant tubes 78a, 78b, and 78c, is drawn through the third stage primary drying tube 60, then through the second stage primary drying tube 50, and finally through the double-head purge vacuum pump 134 before being exhausted from the system. Therefore, as shown, the purge gas used in the primary side only passes through two of the drying tubes and not three as in the preferred embodiment. The ambient purge air for the secondary gas stream is drawn through three of the drying tubes after being dehydrated in its desiccant tubes 138a, 138b, and 138c; first through the second stage secondary drying tube 120, then through the first stage secondary drying tube 110, and finally through the first stage primary drying tube 40. The purge gas is then drawn through the double-head purge vacuum pump 134 and exhausted from the system.

The advantages of the alternative embodiment are that it allows the combined use of the ice bath, a combined inlet for the purge air, and double-head exhaust pumps. All three of these alternative components effectuate savings of space, but yet allow for the drying of two separate gas streams. The two separate gas streams are analyzed separately, and the analysis data may thereafter be compared to one another.

Figure 6:
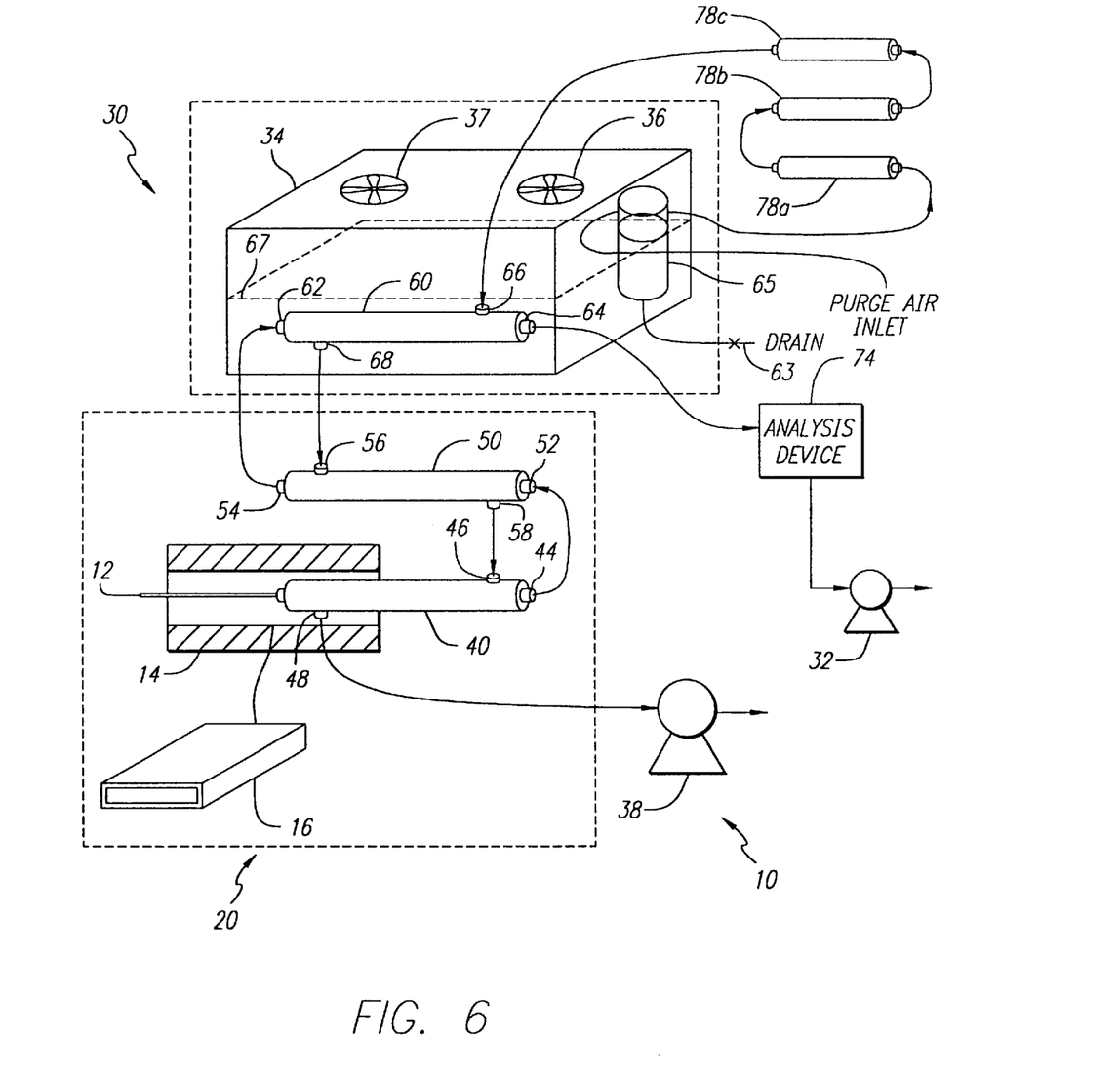
FIG. 6 is a schematic drawing illustrating a third alternative embodiment of the invention in which a water trap is added to increase the efficiency of the drying system.

Referring now to FIG. 6, a third embodiment of the present invention is provided wherein a water trap 65 is included in the water removal system. The water trap 65 comprises a volumetric container device having an inlet and an outlet. The water trap 65 is located in the ice bath 34 such that the water trap 65 is partially submerged below the ice water level 67. The inlet of the water trap 65 is also submerged below the ice water level 67, and is adapted to receive ambient air used as a purge air source. The outlet of the water trap 65 is coupled to the input of the first desiccant tube 78a. The water trap 65 operates to remove moisture from the ambient air prior to entering the three desiccant tubes 78a–78c. This removal of moisture in turn increases the efficiency of the water removal system. More particularly, the ambient air cools by passing through the inlet tubing that is submerged below the ice water level 67, thereby causing moisture in the ambient air to condense and collect within the water trap 65. The water trap 65 may further include a drain pipe 63 extending from the bottom thereof having a check valve that permits the water trap 65 to be periodically purged of collected water.

Having thus described embodiments of the water removal system, it should be apparent to those skilled in the art that certain advantages of the aforementioned system have been achieved. It should also be appreciated that various modifications, adaptations, and alternative embodiments thereof may be made within the scope and spirit of the present invention. For example, a sample water removal system using dry air as the purge gas has been illustrated, but it should be apparent that the inventive concepts described above would be equally applicable to other compact gas drying systems utilizing other types of purge systems to achieve a water vapor pressure gradient differential. The invention is further defined by the following claims.

What is claimed is:

1. A device for removing water from a sample gas stream, comprising:
    a plurality of drying tubes coupled together in series, each one of said plurality of drying tubes further having a first flow path for sample gas and a second flow path for purge gas, said sample gas stream passing through said first flow path of each one of said plurality of drying tubes in series;
    a cooling chamber having an interior volume maintained at a reduced temperature relative to an ambient temperature of said sample gas stream, at least one of said plurality of drying tubes being disposed in said cooling chamber; and
    a purge air source providing a supply of dried air, said purge air source being coupled to said plurality of drying tubes such that dried air passes through said second flow path of each one of said plurality of drying tubes in series;
    wherein, said cooling chamber reduces temperature of said sample gas stream to an approximate dew point of the sample gas to increase drying efficiency of said plurality of drying tubes.

2. The device of claim 1, wherein each of said plurality of drying tubes comprises an ion exchange polymer material exhibiting a selectively high permeability to transfer of water compared to other gaseous compositions.

3. The device of claim 2, wherein said plurality of drying tubes each comprise an outer shell having a sample gas inlet and a sample gas outlet, a plurality of internal tubes comprised of said ion exchange polymer material are disposed within said outer shell extending between said sample gas inlet and said sample gas outlet.

4. The device of claim 3, wherein said plurality of drying tubes each comprise a purge gas inlet and a purge gas outlet, whereby water contained in said sample gas flow passes through sides of said internal tubes and is removed through said purge gas outlet.

5. The device as in claim 1, wherein the cooling chamber further comprises an ice bath.

6. The device of claim 1, further comprising a heater coupled to at least one of said plurality of drying tubes prior to said cooling chamber, said heater being adapted to increase temperature of said sample gas stream above the dew point of the gas stream and accordingly to maintain water contained in said sample gas stream in a vapor state.

7. The device of claim 1, wherein said purge air source further comprises at least one tube containing a desiccant material.

8. The device of claim 1, further comprising a first pump coupled to said first flow path of said plurality of drying tubes and adapted to draw said sample gas therethrough.

9. The device of claim 1, further comprising a second pump coupled to second flow path of said plurality of drying tubes and adapted to draw said purge gas therethrough.

10. The device of claim 1, further comprising a fan coupled to the cooling chamber to provide a source of cooled air.

11. The device of claim 1, wherein said plurality of drying tubes further comprises three drying tubes.

12. The device of claim 1, further comprising a plurality of secondary drying tubes coupled together in series, each one of said plurality of secondary drying tubes further having a first flow path for a secondary sample gas stream and a second flow path for a secondary purge gas, said secondary sample gas stream passing through said first flow path of each one of said plurality of secondary drying tubes in series.

13. The device of claim 12, wherein at least one of said plurality of secondary drying tubes are disposed in said cooling chamber.

14. The device of claim 1, wherein said purge air source further comprises a water trap adapted to receive a flow of ambient air and remove moisture therefrom, said water trap thereby providing said supply of dried air.

15. A device for removing water from a sample gas stream, comprising:
    first means for drying said sample gas stream at a temperature above an approximate dew point of the gas stream, wherein said first drying means further comprises at least one drying tube having a first flow path for sample gas and a second flow path for purge gas, and a heater coupled to said at least one drying tube, said heater being adapted to heat sample gas stream above said sample gas stream dew point to maintain water contained in said sample gas stream in a vapor state; and
    second means for drying said sample gas stream at a temperature below said temperature of said first drying means to approach said dew point, wherein said second drying means further comprises a cooling chamber having an interior volume maintained at a reduced temperature relative to said temperature of said sample gas stream, at least one additional drying tube being disposed in said cooling chamber, said cooling chamber reducing temperature of said sample gas stream to thereby increase drying efficiency of said at least one additional drying tube contained therein.

16. The device of claim 15, wherein said at least one drying tube of each of said first and second drying means each comprises an ion exchange polymer material exhibiting a selectively high permeability to transfer of water compared to other gaseous compositions.

17. The device of claim 16, wherein said at least one drying tube of each of said first and second drying means each comprises an outer shell having a sample gas inlet and a sample gas outlet, a plurality of internal tubes comprised of said ion exchange polymer material are disposed within said outer shell extending between said sample gas inlet and said sample gas outlet.

18. The device of claim 17, wherein said at least one drying tube of each of said first and second drying means each comprises a purge gas inlet and a purge gas outlet, whereby water contained in said sample gas flow passes through sides of said internal tubes and is substantially removed through said purge gas outlet.

19. The device of claim 15, wherein the cooling chamber further comprises an ice bath.

20. A device for removing water from a sample gas stream, comprising:

first means for drying said sample gas stream at a temperature above an approximate dew point of the gas stream;

second means for drying said sample gas stream at a temperature below said temperature of said first drying means to approach said dew point; and a purge air source providing a supply of dried air to said first and second drying means, wherein said purge air source further comprises a water trap adapted to receive a flow of ambient air and remove moisture therefrom, said water trap thereby providing said supply of dried air.

* * * * *